(12) United States Patent
Kelly et al.

(10) Patent No.: US 11,462,306 B2
(45) Date of Patent: Oct. 4, 2022

(54) PRESENTING PATIENT INFORMATION BY BODY SYSTEM

(71) Applicant: CERNER INNOVATION, INC., Kansas City, KS (US)

(72) Inventors: Lisa Kelly, Overland Park, KS (US); Bonnie Smith, Kansas City, MO (US); Mark Davenport, Overland Park, KS (US); Bradley Scott, Overland Park, KS (US)

(73) Assignee: CERNER INNOVATION, INC., Kansas City, KS (US)

( * ) Notice: Subject to any disclaimer, the term of this patent is extended or adjusted under 35 U.S.C. 154(b) by 1200 days.

(21) Appl. No.: 14/585,536

(22) Filed: Dec. 30, 2014

(65) Prior Publication Data

US 2015/0112713 A1    Apr. 23, 2015

Related U.S. Application Data

(62) Division of application No. 13/709,478, filed on Dec. 10, 2012, now abandoned.

(60) Provisional application No. 61/677,551, filed on Jul. 31, 2012, provisional application No. 61/677,550, filed on Jul. 31, 2012.

(51) Int. Cl.

| | |
|---|---|
| *G16H 10/60* | (2018.01) |
| *G06F 3/0481* | (2013.01) |
| *G06F 3/0484* | (2013.01) |
| *G16H 15/00* | (2018.01) |
| *G06F 3/04842* | (2022.01) |

(52) U.S. Cl.
CPC .......... *G16H 10/60* (2018.01); *G06F 3/0481* (2013.01); *G06F 3/04842* (2013.01); *G16H 15/00* (2018.01)

(58) Field of Classification Search
USPC ........................................................ 705/2, 3
See application file for complete search history.

(56) References Cited

U.S. PATENT DOCUMENTS

| | | |
|---|---|---|
| 5,758,095 A | 5/1998 | Albaum et al. |
| 6,802,810 B2 | 10/2004 | Ciarniello et al. |
| 8,165,895 B2 | 4/2012 | Nadas et al. |
| 8,249,896 B1 | 8/2012 | Berger et al. |

(Continued)

FOREIGN PATENT DOCUMENTS

WO    03/025711 A2    3/2003

OTHER PUBLICATIONS

Qing Zeng et al. "A Knowledge-Based, Concept-Oriented View Generation Systemfor Clinical Data," Journal of Biomedical Informatics34,112-128 (2001) (Year: 2001).*

(Continued)

*Primary Examiner* — Joshua B Blanchette
(74) *Attorney, Agent, or Firm* — Shook, Hardy & Bacon L.L.P.

(57) ABSTRACT

Methods, computer systems, and computer storage media are provided for sorting and presenting a patient's medical information by body system. A selection of a body system filter directed to a body system is received, and the patient's medical information is accessed. The selected body system filter is applied to the patient's medical information to generate a set of body-system specific patient information. The body-system specific patient information is presented on a body system view user interface.

15 Claims, 13 Drawing Sheets

(56) References Cited

U.S. PATENT DOCUMENTS

| | | | |
|---|---|---|---|
| 8,301,462 | B2 | 10/2012 | Lipscher et al. |
| 8,392,419 | B2 | 3/2013 | Heaton et al. |
| 8,560,335 | B2 | 10/2013 | Hertel et al. |
| 8,832,558 | B2 | 9/2014 | Cardarelli et al. |
| 2004/0078239 | A1 | 4/2004 | Dacosta |
| 2005/0010442 | A1* | 1/2005 | Kragh .............. G06F 19/322 705/2 |
| 2006/0265249 | A1* | 11/2006 | Follis .............. G06F 19/322 705/3 |
| 2007/0162295 | A1* | 7/2007 | Akhtar .............. G06Q 10/10 705/2 |
| 2008/0040159 | A1* | 2/2008 | Deegan .............. G16H 10/20 705/3 |
| 2008/0243550 | A1* | 10/2008 | Yao .............. G06Q 50/24 705/3 |
| 2009/0276487 | A1* | 11/2009 | Jensen .............. G16H 40/67 709/203 |
| 2010/0050085 | A1 | 2/2010 | Blike et al. |
| 2011/0010195 | A1* | 1/2011 | Cohn .............. G16H 10/60 705/3 |
| 2011/0161107 | A1* | 6/2011 | Goldberg .............. G16H 40/67 705/3 |
| 2011/0179361 | A1* | 7/2011 | Cardarelli .............. A61B 5/0205 715/744 |
| 2012/0253851 | A1 | 10/2012 | Phillips et al. |
| 2013/0191161 | A1 | 7/2013 | Churchwell et al. |
| 2014/0324469 | A1 | 10/2014 | Reiner |
| 2015/0363569 | A1 | 12/2015 | Ryan et al. |

OTHER PUBLICATIONS

Non-Final Office Action dated Apr. 7, 2016 in U.S. Appl. No. 13/709,497, 24 pages.
Non-Final Office Action dated Jul. 5, 2016 in U.S. Appl. No. 13/709,478, 18 pages.
Non-Final Office Action dated Oct. 30, 2014 in U.S. Appl. No. 13/709,497, 17 pages.
Non-Final Office Action dated Jan. 6, 2015 in U.S. Appl. No. 13/709,478, 10 pages.
Final Office Action dated Jun. 9, 2015 in U.S. Appl. No. 13/709,497, 19 pages.
Final Office Action dated Jul. 20, 2015 in U.S. Appl. No. 13/709,478, 15 pages.
Final Office Action dated Oct. 20, 2016 in U.S. Appl. No. 13/709,497, 27 pages.
Final Office Action dated Feb. 1, 2017 in U.S. Appl. No. 13/709,478, 18 pages.
Non-Final Office Action dated Nov. 30, 2017 in U.S. Appl. No. 13/709,478, 14 pages.
Google patents search, Nov. 27, 2017, 2 pages.
"Healthcare Management and Plan and Outcome Goals and Filter", Google Patent Search, Jan. 27, 2017, 2 pages.
"Patient Medical Records and Filtering and Displaying Medications Specific to Conditions", Google Patent Search, Mar. 31, 2016, 2 pages.
Final Office Action received for U.S. Appl. No. 13/709,478, dated Feb. 14, 2020, 19 pages.
Displaying Patient Medical Data and Desired State and Outcome Goal and Comprehensive View of Patient Data, Google Patents Search, Retrieved on Feb. 11, 2020, pp. 1-2.

\* cited by examiner

| DESIRED STATE | | | | | | | PLAN OF CARE | |
|---|---|---|---|---|---|---|---|---|
| ☐ DISPLAY ALL OUTCOMES/INTERVENTIONS | | | | | | | | |
| CURRENT NEURO DESIRED OUTCOMES/INTERVENTIONS | | | | | | | | |
| ▲ UNMET (9) | | | | | | | | |
| NAME | START D/T | END D/T | LAST RESU... | LAST RE... D/T | ASSOCIATE... | | | |
| ✗ ASPIRIN WITHIN 24 HOURS OF ARRIVAL | 03/28/12 16:31 | | NOT MET | 03/28/12 16:42 | AMI CORE MEASURES CARE SET | | | |
| ✗ INITIAL ECG READ BY PHYSICIAN WITHIN 10 MINUTES OF ARRIVAL | 03/28/12 16:31 | | NOT MET | 03/28/12 16:41 | AMI CORE MEASURES CARE SET | | | |
| RESPIRATORY RATE – LESS THAN 24 BR/MIN | 04/03/12 12:24 | 04/03/12 12:24 | | | DAILY OUTCOMES AND INTERVENTIONS | | | |
| PRIMARY PCI BALLOON TIME WITHIN 90 MINUTES OF ARRIVAL | 3/28/12 16:31 | | | | AMI CORE MEASURES CARE SET | | | |
| ADULT SMOKING CESSATION COUNSELING | 03/28/12 16:31 | | | | AMI CORE MEASURES CARE SET | | | |
| LDL CHOLESTEROL ASSESSMENT | 03/28/12 16:31 | | | | AMI CORE MEASURES CARE SET | | | |
| ASPIRIN PRESCRIBED AT DISCHARGE | 03/28/12 16:31 | | | | AMI CORE MEASURES CARE SET | | | |
| ACEI/ARB FOR LVSD AT DISCHARGE | 3/28/12 16:31 | | | | AMI CORE MEASURES CARE SET | | | |
| LIPID LOWERING DISCHARGE MED GOAL | 3/28/12 16:31 | | | | AMI CORE MEASURES CARE SET | | | |
| ▲ MET (0) | | | | | | | | |
| NAME | START D/T | END D/T | LAST RESU... | LAST RE... D/T | ASSOCIATE... | | | |

BODYSYSTEM, ... ×　　　　　　　　　⇦ LIST ⇧ | 📋 RECENT ▾ | NAME
BODYSYSTEM, TWO　　DOB:12/14/1976　　EMR:0001832　　FIN #:000021263
NO KNOWN ALLERGIES　　AGE:35 YEARS　　GENDER:FEMALE　　LOC:4 NORTH – ICU ; 406;
🏠 · 🛆 BODYSYSTEMS MPAGE-SHARE　　　　　　　　　　　　🖨 PRINT  ⏱ 1 MINUTES AGO
⏺ □ ⏺ □ | 🔍 | 150% ▾ | 🗎 ⏺ ○ ○ 🗎
THIS PAGE IS NOT A COMPLETE SOURCE OF VISIT INFORMATION.

| NEURO | CARDIOVAS... | PULMONARY | RENAL-F... | GI-NUTRITION | INTEGUMENT | MUS... | END... | HEM... | INF... | BOD... | ① SUMMARY ~813 |

DAILY OUTCOMES/INTERVENTIONS ~814　　　　ORDERS ~816
☐ DISPLAY ALL OUTCOMES/:　　　　　　　　　◢ MEDICATIONS (4) ~818
◢ CARDIOVASCULAR(8)　　　　　　　　　　　◢ CONTINUOUS (1) ~822
TEMPERATURE ORAL – LESS THAN 37 DEGC　　　① MIDAZOLAM 2 MG + D5W 500 ML 10 ML/HR, IV
PAIN FREE WITH INCREASED ACTIVITY - MET　　　　　LAST DOSE: 4 MG/HR (10/4/2012 16:00)
◢ OTHER(0)　　　　　　　　　　　　　　　◢ SCHEDULED (1) ~824
　　　　　　　　　　　　　　　　　　　　　DILANTIN-125 125 MG, 5 ML, ORAL, TID
　　　　　　　　　　　　　　　　　　　　　　　LAST DOSE:
　　　　　　　　　　　　　　　　　　　　　◢ PRN (1) ~826
　　　　　　　　　　　　　　　　　　　　　TYLENOL 500 MG, 1 TABS, ORAL, Q6HR, PRN: PAIN
　　　　　　　　　　　　　　　　　　　　　　　LAST DOSE:
　　　　　　　　　　　　　　　　　　　　　◢ SUSPENDED (1) ~828
　　　　　　　　　　　　　　　　　　　　　D5W 500 ML + VALIUM 5 MG 10 ML/HR, IV
　　　　　　　　　　　　　　　　　　　　　　　LAST RATE:
　　　　　　　　　　　　　　　　　　　　　◢ NON-MEDICATION ORDERS (12) ~820
　　　　　　　　　　　　　　　　　　　　　◢ LABORATORY (5)
　　　　　　　　　　　　　　　　　　　　　BUN　　　　　　　　ORDERED　　10/04/12 14:36
　　　　　　　　　　　　　　　　　　　　　CBC W/ DIFFERENTIAL　ORDERED　　10/04/12 17:14

MEDICAL DECISION

*ONLY ORDERS AND

SIGN ~830

MENU

| NEURO | CARDIOVASCULAR | | |
|---|---|---|---|
| CURRENT STATE (LAST 24 HOURS) | | | |
| CENTRAL VENOUS PRESSURE ↑99 | SCVO2 45 | | 137  ↑100 |
| SVO2 ↓41 | PULMONARY CAPILLARY WEDGE PRESSURE 11 | | 4   29 |
| RIGHT ATRIAL PRESSURE ↑32 | | | 4500  44 |
| | | | 45 |
| △ PERIPHERALLY INSERTED CATHETER (PICC) DOUBLE MEDIAN ANTEBRACHIAL VEIN RIGHT | | | |
| CENTRAL IV CVP CATHETER WITHDRAW: | 45 | | HCO3 ↑99 |
| CENTRAL IV CVP LINE STATUS: | ACCURATE, OPTIMALLY DAMPED | | PH ART ↑1.3 |
| CENTRAL IV INDICATION: | ADMINISTRATION OF SCLEROSING... | | BLOOD GLUCOSE, ... ↓54 |
| CENTRAL IV UNEXPECTED EVENTS: | CATHETER REMOVE NOT INTACT | | |
| CN V FACIAL SENSATION | CORNEAL REFLEX PRESENT, CORN... | | |
| ENVIRONMENTAL SAFETY IMPLEMENTED | BED IN LOW POSITION, ENCOURAGE... | | |
| GAIT | STAGGERING | | |
| LOSS OF CONSCIOUSNESS | YES | | |
| LOSS OF CONSCIOUSNESS DURATION | 34 MINS | | |
| NEUROLOGICAL SYMPTOMS | CONFUSION/DISORIENTATION, NUM... | | |
| ORIENTATION ASSESSMENT | NOT ORIENTED TO PERSON, NOT O... | | |

| NEURO | CARDIOVASCULAR |
|---|---|

CURRENT STATE (LAST 24 HOURS)

| CENTRAL VENOUS PRESSURE ↑99 | SCVO2 45 |
|---|---|
| SVO2 ↓41 | PULMONARY CAPILLARY WEDGE PRESSURE 11 |
| RIGHT ATRIAL PRESSURE ↑32 | |

137  ↑100
4  29
4500  44
  45  ↑99

| HCO3 | ↑99 |
| PH ART | ! 1.3 |
| BLOOD GLUCOSE, ... | ↓54 |

△ PERIPHERALLY INSERTED CATHETER (PICC) DOUBLE MEDIAN ANTEBRACHIAL VEIN RIGHT
CENTRAL IV CVP CATHETER WITHDRAW: 45
CENTRAL IV CVP LINE STATUS: ACCURATE, OPTIMALLY DAMPED
CENTRAL IV INDICATION: ADMINISTRATION OF SCLEROSING...
CENTRAL IV UNEXPECTED EVENTS: CATHETER REMOVE NOT INTACT
CN V FACIAL SENSATION | CENTRAL IV INDICATION: ADMINISTRATION OF SCLEROSING AGENTS, CENTRAL VENOUS PRESSURE MEASUREMENT (11/12/2012 20:02)
ENVIRONMENTAL SAFE
GAIT  STAGGERING
LOSS OF CONSCIOUSNESS  YES
LOSS OF CONSCIOUSNESS DURATION  34 MINS
NEUROLOGICAL SYMPTOMS  CONFUSION/DISORIENTATION, NUM...
ORIENTATION ASSESSMENT  NOT ORIENTED TO PERSON, NOT O...

PRESENTING PATIENT INFORMATION BY BODY SYSTEM

CROSS-REFERENCE TO RELATED APPLICATIONS

This application is a Divisional Application of U.S. application Ser. No. 13/709,478, filed Dec. 10, 2012, and entitled "Presenting Patient Information by Body System," which claims the benefit of priority of U.S. Provisional Application No. 61/677,550, filed Jul. 31, 2012 and entitled "Presenting Patient Information by Body System;" and U.S. Provisional Application No. 61/677,551, filed Jul. 31, 2012 and entitled "Presenting Medication Information by Body System." The entirety of the aforementioned applications are incorporated by reference herein.

BACKGROUND

Traditionally a patient's medical information is sorted and presented by data type such as laboratory results, medications, or clinician notes, or by user actions such as a nurse documentation view or a test ordering view. The type of computer application program may also determine how medical information is sorted and presented. For example, an image viewing application classifies medical information based on medical images and presents those images on a user interface.

Although these different ways of sorting and presenting medical information meet clinician needs in a wide array of circumstances, currently there is no effective way to provide a comprehensive view of a patient's medical information based on body system such as, for example, medical information related to the patient's cardiovascular system or the patient's gastrointestinal system. This may be especially problematic in an intensive care unit (ICU) setting where clinicians typically care for patients with multiple medical problems that encompass multiple different body systems.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer storage media for sorting and presenting a patient's medical information, including medication order information, by body system. A patient's medical information is accessed and body system filters are applied to the information to generate multiple sets of body-system specific patient information. The body-system specific patient information is presented on an easy-to-use user interface (UI).

The user can select a particular body system on the UI by utilizing a variety of body system filter tabs. Once selected, the patient information related to the selected body system may be presented, in part, in a current state display area configured to present current information related to the patient's body system, and in an order display area configured to present current orders, such as medication orders, related to the patient's body system. Further, information may also be presented in an outcome goals display area that presents outcome goals related to the selected body system.

The user can add, delete, and/or modify the information directly from the UI, and, even more, a summary page is automatically generated that reflects any changes to the body-system specific patient information and/or outcome goals made by the user. The user can additionally automatically generate a clinical note that summarizes any modifications that have been made to the body-system specific information.

BRIEF DESCRIPTION OF THE DRAWINGS

Embodiments are described in detail below with reference to the attached drawing figures, wherein:

FIG. 3 is an exemplary graphical user interface presenting patient information by body system in accordance with an embodiment of the present invention;

FIG. 4 is an exemplary graphical user interface presenting a detailed view of a current state of body-system specific patient information in accordance with an embodiment of the present invention;

FIG. 5 is an exemplary graphical user interface presenting a detailed view of order information based on body system in accordance with an embodiment of the present invention;

FIG. 6 is an exemplary graphical user interface presenting a detailed view of order information including icons indicative that an action has been taken with respect to one or more of the orders in accordance with an embodiment of the present invention;

FIG. 7 is an exemplary graphical user interface presenting a detailed view of outcome goals related to a body system in accordance with an embodiment of the present invention;

FIG. 8 is an exemplary graphical user interface presenting a summary page indicating actions that have been taken with respect to the body-system specific patient orders and outcome goals in accordance with an embodiment of the present invention;

FIG. 13 is an exemplary graphical user interface presenting a clinical note that summarizes actions that have been taken with respect to the body-system specific orders and outcome goals in accordance with an embodiment of the present invention; and FIGS. 14-15 are exemplary graphical user interfaces presenting a current state of body-system specific patient information in accordance with embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer storage media for sorting and presenting a patient's medical information, including medication order information, by body system. A patient's medical information is accessed and body system filters are applied to the information to generate multiple sets of body-system specific patient information. The body-system specific patient information is presented on an easy-to-use user interface (UI).

The user can select a particular body system on the UI by utilizing a variety of body system filter tabs. Once selected, the patient information related to the selected body system may be presented, in part, in a current state display area configured to present current information related to the patient's body system, and in an order display area configured to present current orders, such as medication orders, related to the patient's body system. Further, information may also be presented in an outcome goals display area that presents outcome goals related to the selected body system. The user can add, delete, and/or modify the information directly from the UI, and, even more, a summary page is automatically generated that reflects any changes to the body-system specific patient information and/or outcome goals made by the user. The user can additionally automatically generate a clinical note that summarizes any modifications that have been made to the body-system specific information.

Figure 1:
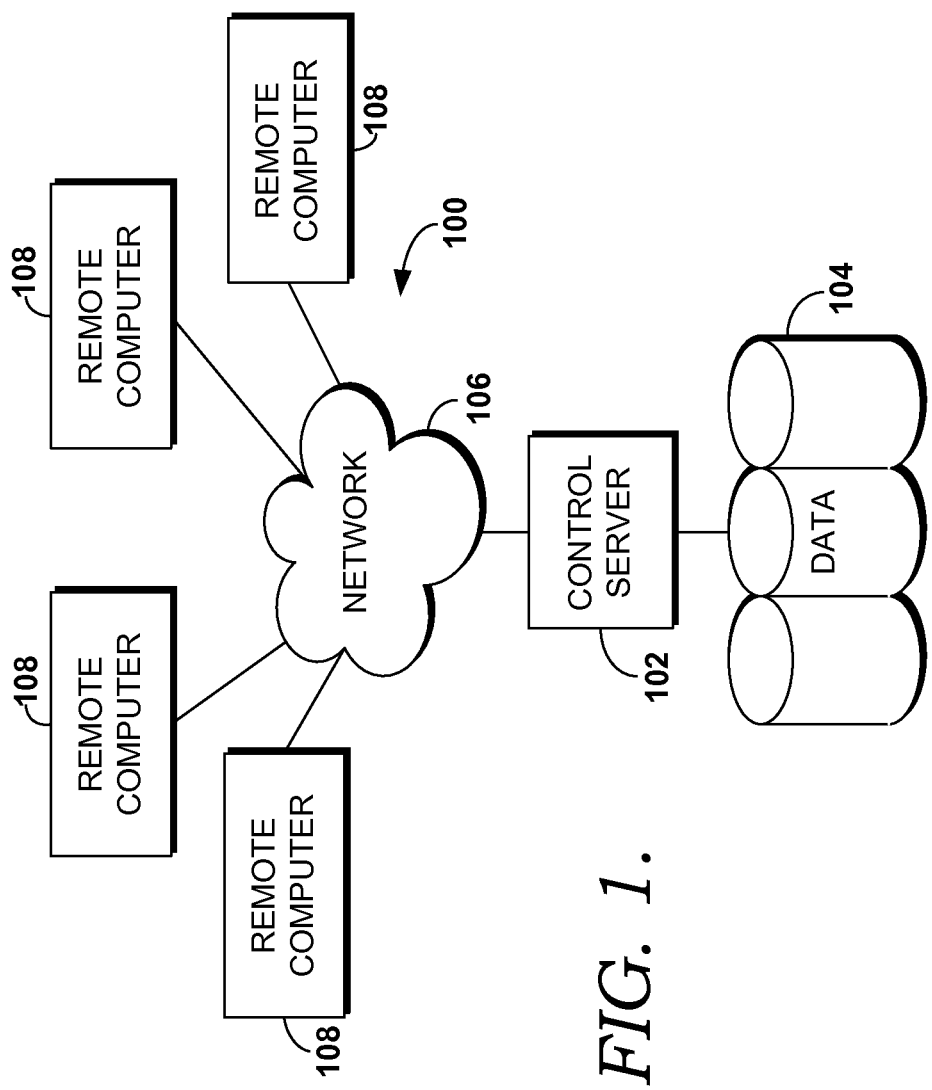
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
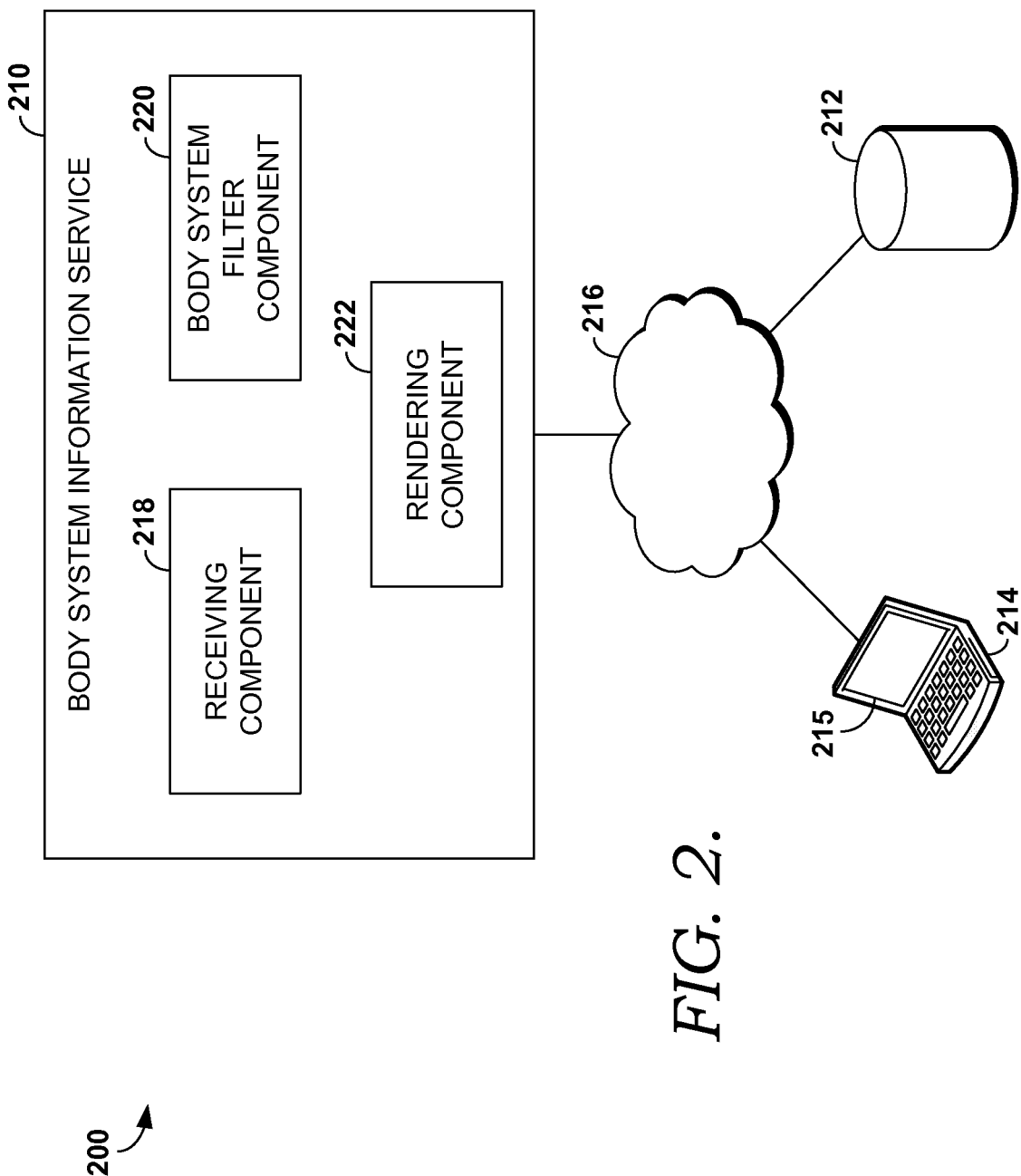
FIG. 2 is a block diagram of an exemplary system for presenting patient information by body system suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a body system information service 210, a data store 212, and an end-user computing device 214 with a display screen 215 all in communication with one another via a network 216. The network 216 may include, without limitation, one or more local area networks (LANs) and/or wide area networks (WANs). Such networking environments are commonplace in offices, enterprise-wide computer networks, intranets and the Internet. Accordingly, the network 216 is not further described herein.

In some embodiments, one or more of the illustrated components/modules may be implemented as stand-alone applications. In other embodiments, one or more of the illustrated components/modules may be integrated directly into the operating system of the body system information service 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the body system information service 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the body system information service 210. The information stored in association with the data store 212 is configured to be searchable for one or more items of information stored in association therewith. The information stored in association with the data store 212 may comprise general information used by the body system information service 210.

The data store 212 may store electronic medical records (EMRs) of patients associated with one or more healthcare facilities. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

Additionally, the data store 212 may store information concerning decision-support algorithms, outcome-related goals, reference materials, standards of care, recommendation protocols, and the like. This information may be specific to a healthcare facility, or the information may be promulgated by, for example, nationally-recognized medical organizations or governing bodies. Information stored in the data store 212 may also include medication information including therapeutic classes of medications and medications stocked by any particular healthcare facility's pharmacy.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the body system information service 210, the end-user computing device 214, and/or any combination thereof.

As shown, the end-user computing device 214 includes a display screen 215. The display screen 215 is configured to display information to the user of the end-user computing device 214, for instance, information relevant to communications initiated by and/or received by the end-user computing device 214, medical information sorted and presented by body system, medication order information sorted and presented by body system, and/or the like. Embodiments are not intended to be limited to visual display but rather may also include audio presentation, combined audio/visual presentation, and the like. The end-user computing device 214 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions.

Components of the body system information service 210 may include a processing unit, internal system memory, and a suitable system bus for coupling various system components, including one or more data stores for storing information (e.g., files and metadata associated therewith). The body system information service 210 typically includes, or has access to, a variety of computer-readable media.

The computing system environment 200 is merely exemplary. While the body system information service 210 is illustrated as a single unit, it will be appreciated that the body system information service 210 is scalable. For example, the body system information service 210 may in actuality include a plurality of computing devices in communication with one another. Moreover, the data store 212, or portions thereof, may be included within, for instance, the body system information service 210 as a computer-storage medium. The single unit depictions are meant for clarity, not to limit the scope of embodiments in any form.

As shown in FIG. 2, the body system information service 210 comprises a receiving component 218, a body system filter component 220, and a rendering component 222. In some embodiments, one or more of the components 218, 220, and 222 may be implemented as stand-alone applications. In other embodiments, one or more of the components 218, 220, and 222 may be integrated directly into the operating system of a computing device such as the remote computer 108 of FIG. 1. It will be understood that the components 218, 220, and 222 illustrated in FIG. 2 are exemplary in nature and in number and should not be construed as limiting. Any number of components may be employed to achieve the desired functionality within the scope of embodiments hereof.

The receiving component 218 is configured to receive user selections, commands, filters, tags, requests, or inputs. Additionally, the receiving component 218 is configured to receive updates to outcome-related goals and/or updates to a patient's EMR. The updates may occur when a healthcare facility or clinician modifies or adds outcome-related goals, or when a clinician updates a patient's EMR with new information. User selections and/or requests may include requests for one or more body system views of a patient's medical information including a patient's medication order information.

The body system filter component 220 is configured to apply one or more user-selected body system filters to, for example, medical information in a patient's EMR. The EMR, in turn, may be stored in association with the data store 212. In one aspect, the body system filter component 220 is configured to identify medical information that falls within a predetermined time frame and apply the one or more body system filters to the medical information within the time frame. Such time frames may include medical information collected over the past hour, the past 24 hours, the past 1000 hours, and any time frame in between.

As well, the body system filter component 220 is configured to apply one or more user-selected body system filters to, for example, outcome-related goals stored in association with the data store 212. Outcome-related goals represent a desired state for a patient and may include healthcare facility-specific outcome-related goals, clinician-specific outcome-related goals, and/or outcome-related goals recommended by national or state healthcare governing bodies. Outcome-related goals encompass a wide variety of goals ranging from nutrition goals, patient education goals, physiologic parameter goals, lab value goals, assessment goals, and the like.

Body system filters applied by the body system filter component 220 are directed to particular body systems. Body systems may include the following: neurological, cardiovascular, lungs, renal-fluid, GI-nutrition, integument, musculoskeletal, endocrine, hematology, inflammation, immunocompromised, and the like. Body system filters may also include user-configurable body system filters. In this instance, a user may comprise a clinician or a healthcare facility.

By applying one or more of the user-selected body system filters to a patient's medical information and to outcome-related goals, the body system filter component 220 generates sets of body-system specific patient information and outcome-related goals. Body-system specific patient information may include clinical observation information related to the body system, physiologic information related to the body system, medication and non-medication order information related to the body system, and the like.

The rendering component 222 is configured to render and present the body-system specific information and the outcome goals on a user interface (UI). The body-system specific information may be presented in a current state display area that presents current clinical observation information, and current physiologic information including laboratory values related to a body system. The body-system specific information may additionally be presented in an order display area that presents current medication and non-medication orders for the patient related to the body system. The body-system specific outcome goals may be presented in an outcome goals display area. The information on the UI may be presented in conjunction with a variety of icons. Such icons can include status icons that indicate that a particular piece of information is new or has been modified in some way. Icons may also include user action icons. By selecting one of the user actions icons, a user can initiate an action for a data item(s). For example, a user action for a medication order may include a suspend action, a modify action, or a delete/discontinue action.

In one aspect, the rendering component 222 is configured to present medical information and outcome goals information for one body system at a time. In another aspect, the rendering component 222 is configured to simultaneously present medical information and outcome goals for more than one body system. In this instance, information for a first body system may be visually demarcated in some manner from information for a second body system, and so on.

The rendering component 222 is further configured to generate one or more summary pages that summarize any changes, deletions, or modifications made by a user to information pertaining to a particular body system. In one aspect, a different summary page is generated for each body system to which changes to information were made. In another aspect, a single summary page may be generated that summarizes changes made to more than one body system. Within this single summary page, changes may be categorized by body system. Additionally, the rendering component 222 is configured to automatically generate a signed clinical note summarizing any changes made by a user to body system information. At least a portion of the clinical note may be generated using body-system specific information and/or outcome goals that were tagged by the user. For example, when a user is viewing patient information related to a particular body system, the user can tag various data items such as a clinical observation, a lab result, an outcome goal, and/or a medication. The rendering component 222 uses these tagged items to automatically generate at least a part of a clinical note, and the user can input additional information to complete the note.

Figure 3:
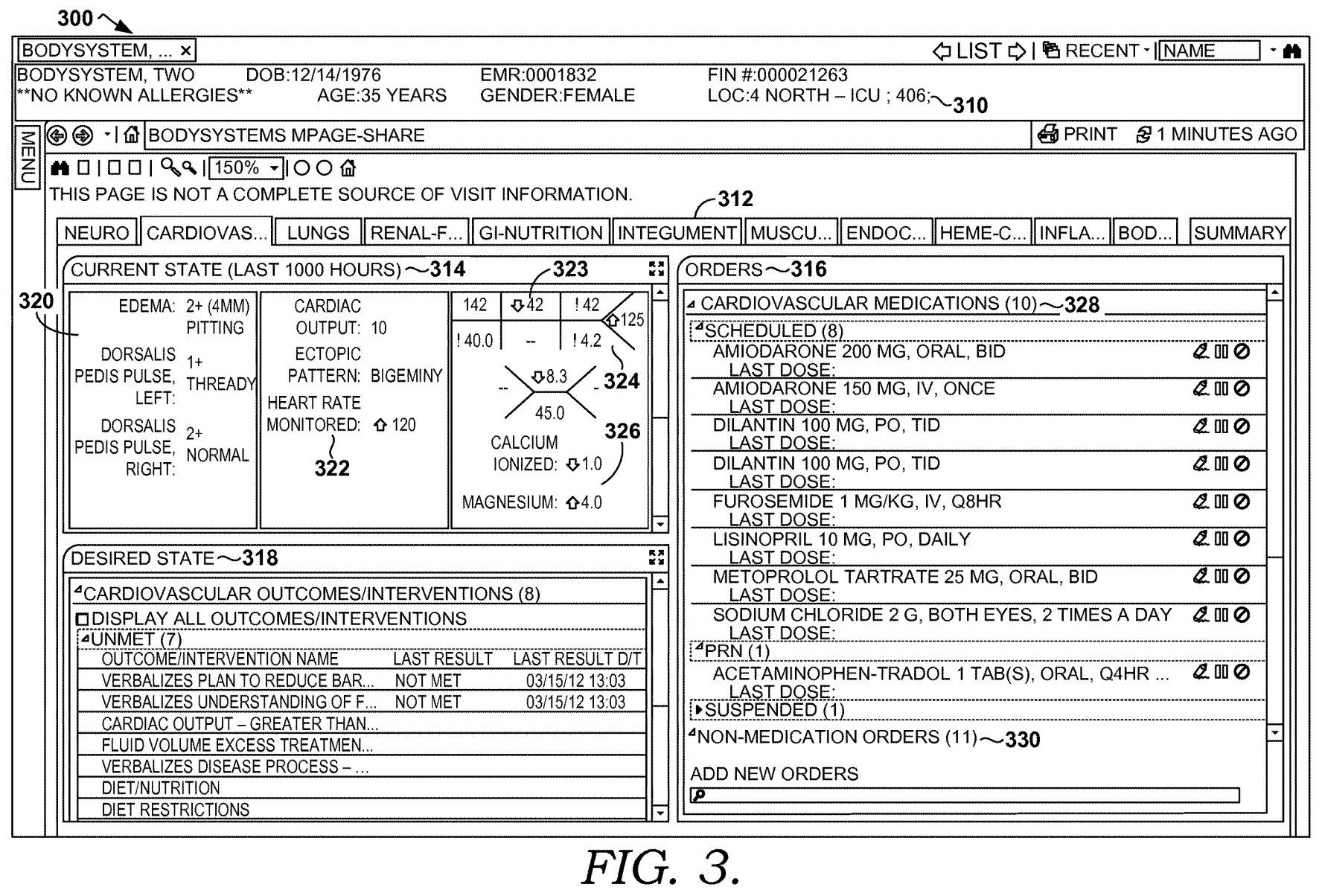
Figure 13:
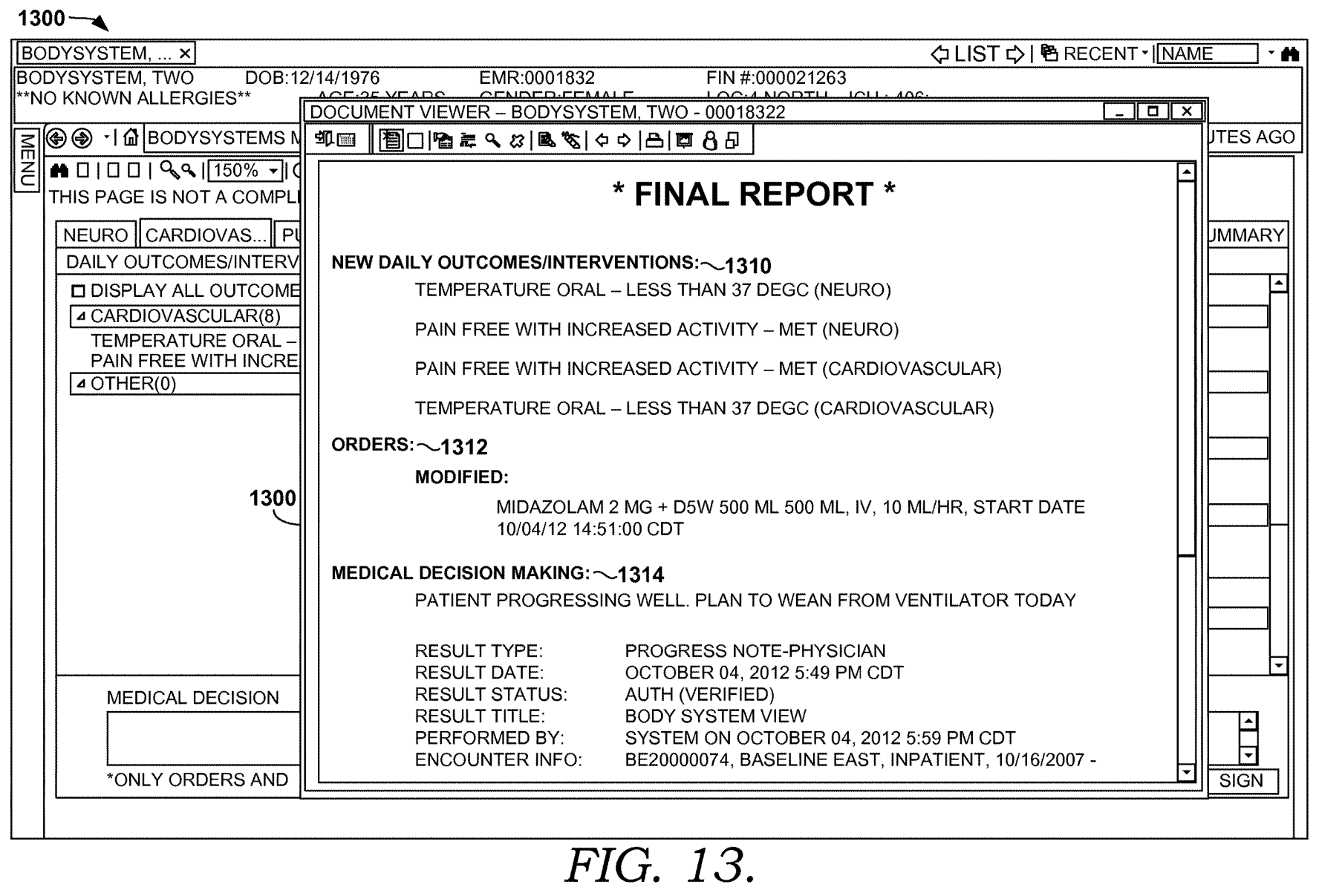

Turning now to FIGS. 3-8 and 13-15, FIGS. 3-8 and 14-15 depict exemplary graphical user interfaces (GUIs) illustrating the presentation of medical information by body system, and FIG. 13 depicts an exemplary clinical note that summarizes any changes or modifications made to the body-system specific information. FIG. 3 depicts a body system view 300 of a patient's medical information and outcome goals related to the selected cardiovascular system. The body system view 300 includes a patient identification area 310 that presents information identifying the patient. A series of selectable tabs are included in a tab selection area 312. Each tab corresponds to a different body system, and a summary tab summarizes any changes and/or modifications made to the body-system specific information. Further, at least one or more of the tabs is configurable by a user. Upon selection of a body system tab in the tab selection area 312, patient information, including outcome goals, related to the selected body system is presented.

The body system view 300 further includes a current state display area 314 that presents current body-system specific patient information over a predetermined time frame (in this case, the time frame is the last 1000 hours). The current state display area 314 may be subdivided into a clinician observation area 320, a physiology display area 322, and a lab result display area 323. The clinician observation area 320 is configured to present clinical observations related to the patient and the selected body system. The observations are generally subjective in nature and vary depending on the body system. The physiology display area 322 is configured to present objective physiological measurements related to the selected body system. The measurements may include results from various procedures or exams. The lab result display area 323 can be further subdivided into a generalized lab result display area 324 and a body-system specific lab result area 326. As the names imply, the generalized lab result display area 324 presents lab results that are useful or important across multiple body systems, and, hence, the information in this area 324 will generally be the same regardless of which body system filter tab is selected. The body-system specific lab result area 326 presents lab values that are specific to the selected body system. The information presented in the body-system specific lab result area 326 may also be presented in association with a different body system if the information is pertinent to that body system as well.

FIGS. 14-15 depict alternative representations of a current state display area 1410. The current state display area 1410 may present substantially the same information as the current state display area 314 of FIG. 3, but the layout of the information may be different (i.e., using a two-column presentation of information instead of a three-column presentation of information) in order to efficiently utilize screen real estate. Although FIGS. 14-15 depict the current state display area 1410 in isolation, it is to be understood that the current state display area 1410 may be presented in association with an order display area and an outcome goals display area (discussed in more depth below).

The current state display area 1410 includes a physiology display area 1412 similar to the physiology display area 322 of FIG. 3, a clinician observation display area 1414 similar to the clinician observation display area 320 of FIG. 3, and a lab result display area 1416 similar to the lab result display area 323 of FIG. 3. Similar to the current state display area 314 of FIG. 3, the physiology display area 1412 is configured to present objective physiological measurements related to the selected body system (the neuro system in this case). The measurements may include results from various procedures or exams. The clinician observation area 1414 is configured to present clinical observations related to the patient and the selected body system. The observations are generally subjective in nature and vary depending on the body system. The lab result display area 1416 can be further subdivided into a generalized lab result display area 1418 and a body-system specific lab result area 1420. As the names imply, the generalized lab result display area 1418 presents lab results that are useful or important across multiple body systems, and, hence, the information in this area 1418 will generally be the same regardless of which body system filter tab is selected. The body-system specific lab result area 1420 presents lab values that are specific to the selected body system. The lab values presented in the body-system specific lab result area 1420 may also be presented in association with another body system if the lab values are pertinent to that body system as well.

FIG. 15 presents the same graphical user interface as FIG. 14 (e.g., the current state display area 1410), and includes additional information 1520 that may be presented when a user selects an item, such as a physiologic result item 1522, in the current state display area 1410. The item 1522 may be selected by the user clicking on or hovering over the item 1522. Other ways known in the art for selecting an item on a graphical user interface are contemplated as being within the scope of the invention. The information 1520 may include clinician comments along with a date and time when the comment was received. The information associated with an item may vary depending on the item selected. For instance, selection of a physiologic result such as physiologic result 1528 or a lab value such as lab value 1524 may initiate a presentation of a date and time when the physiologic result 1528 or the lab value 1524 was documented, a normal reference range for the result 1528 or the value 1524, a critical reference range for the result 1528 or the value 1524, an indication whether the result 1528 or the value 1524 has been reviewed and/or verified, and the like. Selection of a clinical observation, such as clinical observation 1526 may initiate presentation of clinician and/or caregiver comments regarding the observation 1526 along with a date and time when the comments were documented.

Turning back to FIG. 3, the body system view 300 also includes an order display area 316 configured to present current medication orders 328 for the patient that are specific to the selected body system; the order display area 316 also presents non-medication orders 330. The non-medication orders 330 may include orders for labs, orders for exams or procedures, and the like. In one aspect, the non-medication orders 330 are specific to the selected body system. In an alternative aspect, the non-medication orders 330 are general in nature and are presented regardless of the body system filter selected. The non-medication orders 330 may be further subdivided into general categories such as laboratory orders, exam orders, procedure orders, and the like. Another category may include non-medication orders that have been discontinued within the past 24 hours.

As mentioned, the medication orders 328 presented in the order display area 316 are related to the selected body system. In other words, medications presented in the order display area 316 are targeted to some aspect of the selected body system (e.g., organ, disease condition, physiologic process, etc.) and may encompass multiple therapeutic classes of drugs. Further, a medication in the medication order area 328 may be carried over to different body systems if that medication is used to treat some aspect of the different body system. For instance, the medication furosemide may be used to treat disease conditions that affect both the cardiovascular system and the renal-fluid system. Thus, the medication order for furosemide would be presented in relation to both the cardiovascular body system view and the renal-fluid body system view.

The medication orders 328 may be subdivided into those that are continuously administered (e.g., by intravenous administration), administered on a scheduled basis (e.g., twice a day), administered as needed (i.e., for pain relief), medications that have been suspended, and medications that have been discontinued within, for example, the past 24 hours. Each medication order may include information such as medication name, dosage amount, frequency of dosage, route of administration, ordering clinician, date when order was entered, date when order is set to expire (if any), reason for order, clinician notes related to the order, and the like.

The body system view 300 also includes an outcome goals display area 318 configured to present a set of outcome goals related to the selected body system. As mentioned, outcome goals represent a desired state for the patient and include objective and subjective goals. Additional information concerning the presentation of outcome goals is provided in relation to FIG. 7.

Figure 4:
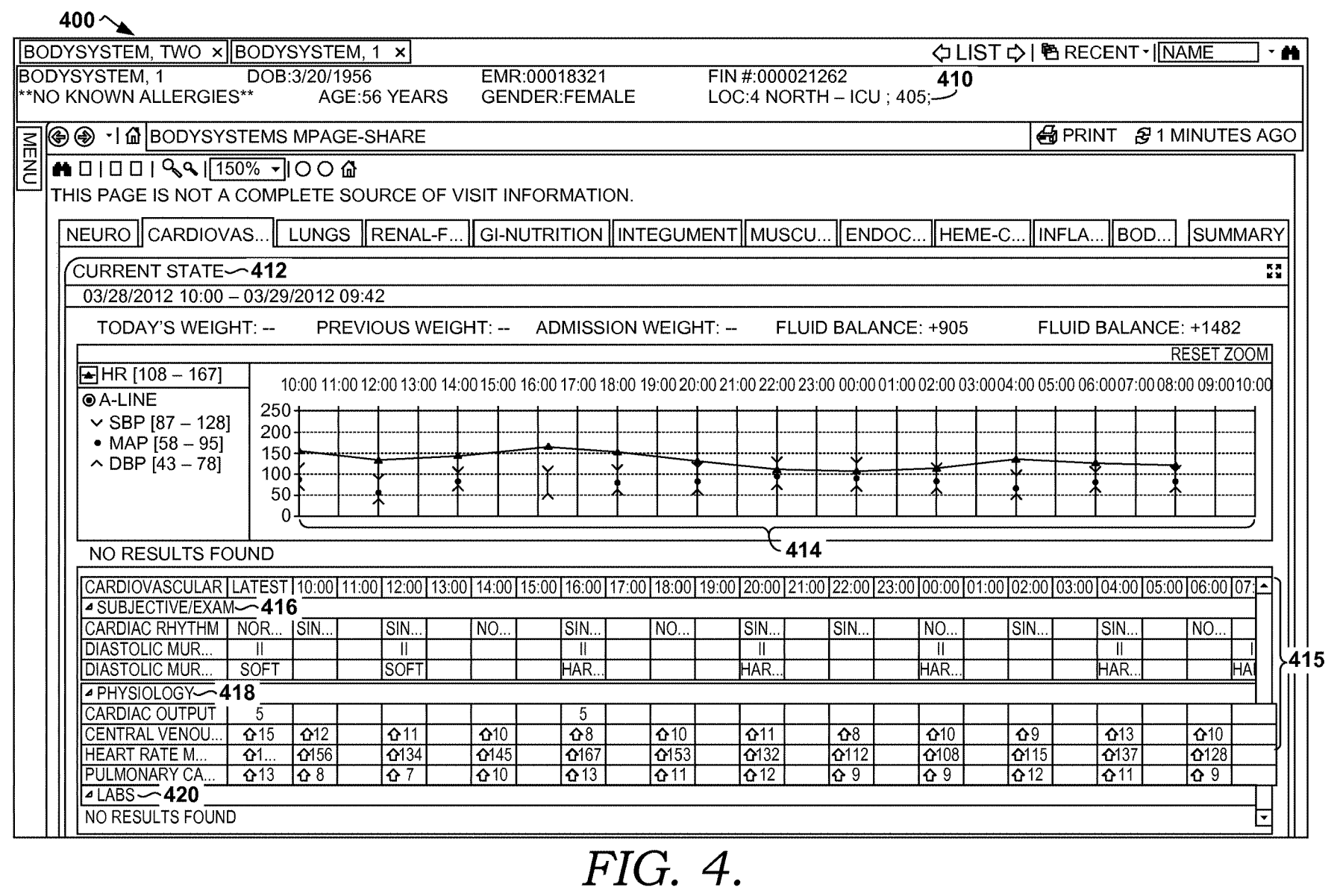

Turning now to FIG. 4, FIG. 4 is an exemplary graphical user interface (GUI) 400 illustrating a detailed view of a current state display area such as the current state display area 314 of FIG. 3. Like the body system view 300 of FIG. 3, the GUI 400 is shown as presenting information related to a selected cardiovascular filter tab. The GUI 400 includes a patient identification area 410 similar to the patient identification area 310 of FIG. 3. The GUI 400 also includes a detailed view of the current state display area 412. This view may be initiated by selecting, for example, the current state display area 314 of FIG. 3. The current state display area 412 includes a trending graph 414 that presents heart rate and blood pressure information over the past 24 hours in a graph form. In one aspect, the trending graph 414 of heart rate and blood pressure information is presented across all of the body systems. In another aspect, the information contained in the trending graph 414 is dependent upon the selected body system. Other information presented in association with the trending graph 414 that may be body-system specific may include, for example, fluid intake/output information, EKG information, respiratory rate and/or tidal volume information, electrolyte or marker level information, subjective pain scale information, hormone levels, and the like.

The GUI 400 further includes trending information area 415. The trending information area 415 may include a trending subjective information area 416, a trending physiologic area 418, and a trending lab result area 420. Information in the trending information area 415 is presented in a table form and represents data collected over, for example, the past 24 hours. The amount of time over which data is presented is configurable by the user. For instance, the user may select to view trending information collected over the past hour if the information is rapidly changing. Alternatively, the user may select to view trending information collected over a longer time frame if the information slowly changes.

Information in the trending subjective information area 416 may include information that represents all or part of the clinical observation information presented in the clinical observation information area 320 of FIG. 3. Information in the trending physiologic area 418 may represent all or a portion of the physiologic information presented in the physiologic display area 322 of FIG. 3. Like the subjective information 416, the physiologic information 418 represents data collected over, for example, the past 24 hours or another time period selected by a user. Information in the trending lab result area 420 may represent all or a portion of the lab results shown in the lab result display area 323 of FIG. 3. Again, the lab result information may be over a 24 hour time period or another time period selected by the user.

Figure 5:
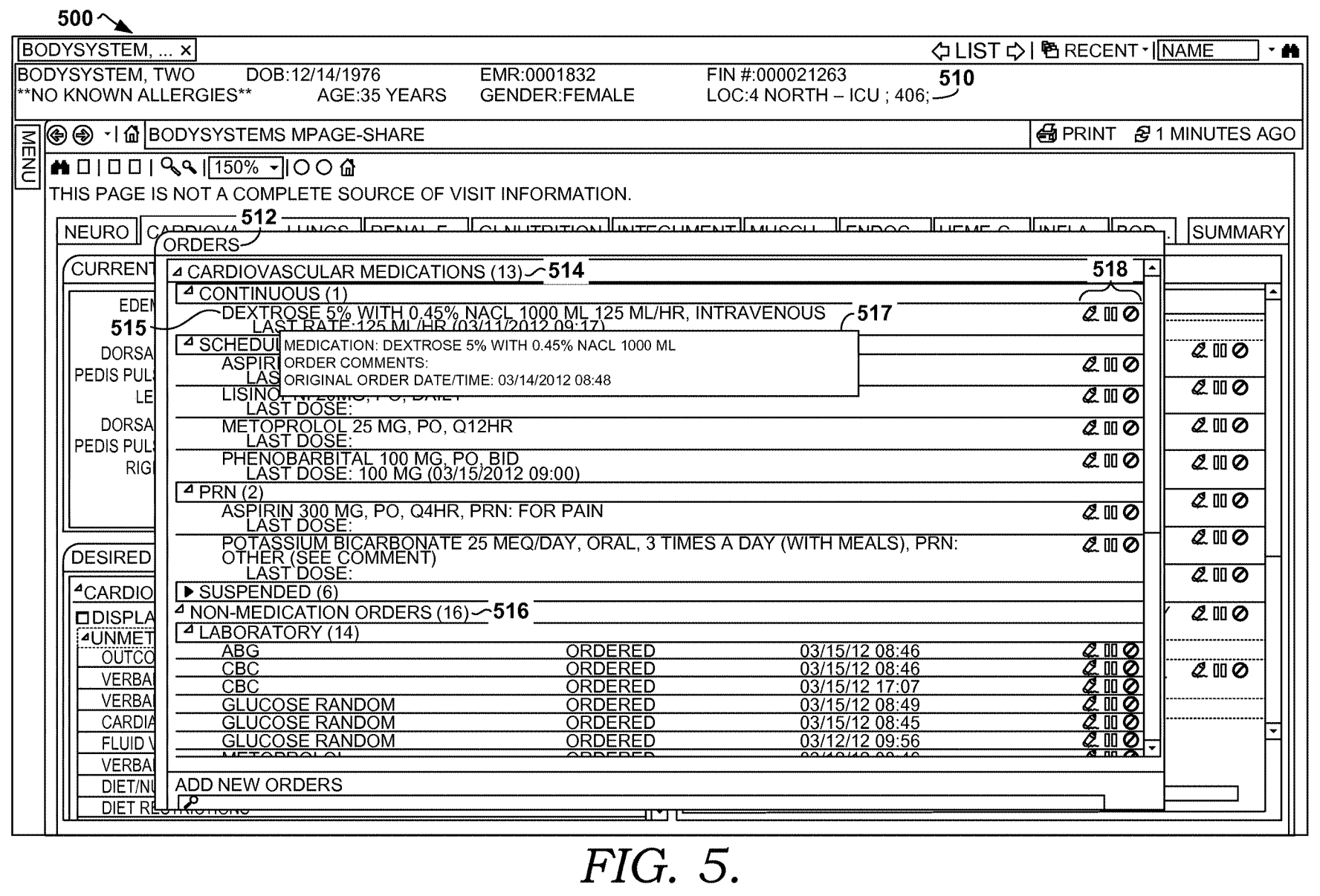

FIG. 5 is an exemplary graphical user interface (GUI) 500 illustrating a detailed view of an order display area 512; the detailed view may be initiated by a user selecting, for example, the order display area 316 of FIG. 3. Like the body system view 300 of FIG. 3, the GUI 500 is shown as presenting information related to a selected cardiovascular filter tab. The GUI 500 includes the order display area 512 similar to the order display area 316 of FIG. 3. In one aspect, the order display area 512 only includes a medication order display area 514. In another aspect, the order display area 512 includes the medication order display area 514 and a non-medication order display area 516. As mentioned above, the medication order display area 514 presents medication information specific to the selected body system (e.g., the cardiovascular system). The medication information may include medication name, dosage amount, dosage frequency, and route of administration. As shown in area 517, a user can hover over one of the medication orders to initiate the presentation of more detailed information including order comments, date of order, date of expiration, and the like. The non-medication order display area 516 presents order information such as lab orders, procedure orders, consult orders, and the like. In one aspect, the order information presented in the non-medication order display area 516 is general in nature and is presented regardless of the body system filter selected. In another aspect, the order information in the non-medication order display area 516 is filtered according to the selected body system. Any and all such aspects are contemplated as being within the scope of the invention.

The order display area 512 may include one or more user action icons shown in area 518. Each of the user action icons shown in the area 518 is selectable and enables a user to modify, suspend, and/or cancel or discontinue an order.

Figure 6:
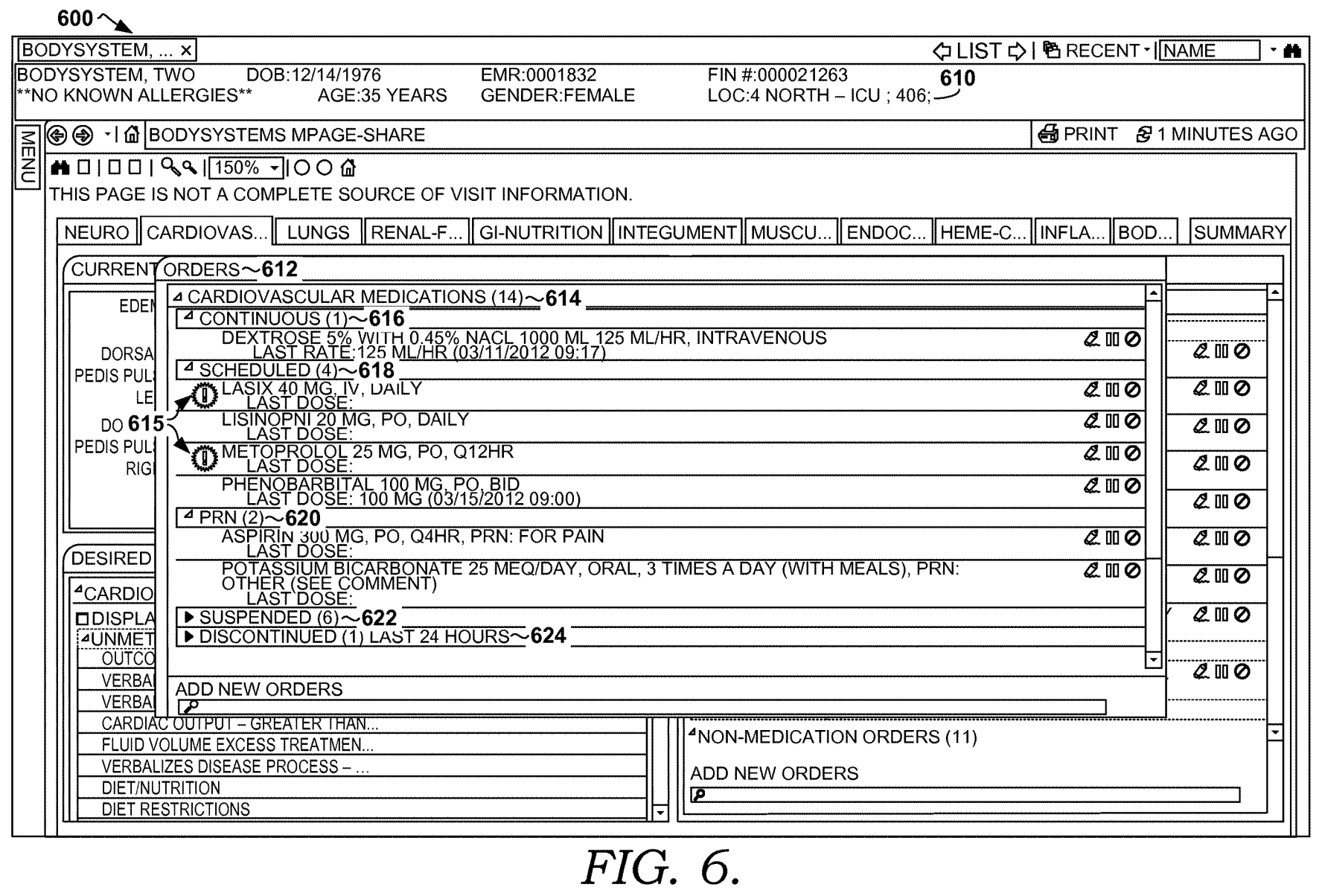

Once an action has been taken with respect to an order, a status icon may be presented in association with the order. An example of status icons is shown in FIG. 6. FIG. 6 illustrates the order display area 512 of FIG. 5 (now labeled as order display area 612) after a user action has been initiated for one or more of the medication orders. As can be seen in medication order display area 614, status icons 615 are presented in conjunction with a medication order for lasix and a medication order for metoprolol. Information regarding the nature of the action taken for lasix and metoprolol may be found on a summary page as explained in more detail with respect to FIG. 8.

Continuing with FIG. 6, the medication order display area 614 may be further subdivided into a continuous category 616, a scheduled category 618, a PRN category 620, a suspended category 622, and a discontinued within the last 24 hours category 624. The categories 616, 618, 620, 622, and 624 are based on the frequency of administration, and each of the categories may include a numerical indicator indicating the number of medication orders within that particular category. The categories 616, 618, 620, 622, and 624 are exemplary in nature, and it is contemplated that other categories can be used for categorizing medication orders within a particular body system.

Turning now to FIG. 7, FIG. 7 depicts an exemplary graphical user interface (GUI) 700 illustrating a detailed view of an outcome goals display area 712 such as the outcome goals display area 318 of FIG. 3. The GUI 700 may be initiated by a user selecting, for example, the outcome goals display area 318 of FIG. 3. Like the body system view 300 of FIG. 3, the GUI 700 is shown as presenting outcome goals related to a selected cardiovascular filter tab. The outcome goals display area 712 includes an option 714 by which all outcome goals and interventions for the selected body system are presented. In the alternative, a user can select to view "met" outcome goals 726 or "unmet" outcome goals 716 (or other logical categories). Each outcome goal may include a descriptive name 718, a start date/time, an end date/time, an indicator 722 of whether the outcome goal was met/not met (and an associated reason why the outcome goal was met/not met if applicable), a last result date/time, and an associated plan 724. If an outcome goal has not been met, a status indicator 720 may be presented in association with the particular outcome goal. The decision as to whether an outcome goal has been met/not met may be made on system level. For example, if an outcome goal requires that a measured value fall within a predetermined range, the system automatically makes this determination and presents the associated met/not met indicator. Additionally, the decision as to whether the outcome goal has been met/not met may be manually inputted by a clinician caring for the patient along with any comments regarding the outcome goal. Goals in the outcome goals display area 712 are automatically updated as new outcome goals are added by, for example, a healthcare facility or a clinician. Further, clinicians can directly add or modify an outcome goal in the outcome goals display area 712.

FIG. 8 depicts an exemplary graphical user interface (GUI) 800 illustrating a summary page 812 that is initiated upon selection of a summary tab 813. The summary page 812 presents information concerning any modifications made by the user to body-system specific information. In one aspect, a separate summary page is generated for each body system. In another aspect, the summary page 812 may include multiple body systems, but the changes for each body system are demarcated in some manner using, for example, headings are parenthetical qualifiers.

The summary page 812 includes a modification to outcome goals area 814 that reflects any changes to the outcome goals. The changes may include the deletion or addition of an outcome goal by a clinician or healthcare facility, any comments regarding a particular outcome goal, and other related information. Changes to the outcome goals may be presented by body system. For example, with respect to the summary page 812, modifications to the outcome goals for the cardiovascular system are presented in the area 814. The area 814 may further include any changes to the outcome goals for a different body system such as, for example, the GI-nutrition system. In an alternative aspect, the changes to the outcome goals for the different system may be presented on a separate summary page. Any and all such aspects are contemplated as being within the scope of the invention.

The summary page 812 also includes a modification to orders area 816 that summarizes any actions and/or modifications that have been taken with respect to patient orders. The summary of actions and/or modification that have been taken with respect to patient orders may be specific to a particular body system or may represent a summary of actions and/or modifications that are independent of body system. The modification to orders area 816 is subdivided into a modification to medication orders area 818 and a modification to non-medication orders 820. The modification to medication orders area 818 is further subdivided by type of medication such as continuous 822, scheduled 824, PRN 826, and suspended 828. The summary page further includes a sign area 830. By selecting the sign area 830, a clinician can initiate the presentation of a signed clinical note that includes, in part, orders and outcomes/interventions that have been modified in some way.

Turning to FIG. 13, FIG. 13 depicts an exemplary clinical note 1300 generated in response to, for example, a user selecting the sign area 830 on the summary page 812. The clinical note 1300 summarizes any changes, modifications, and/or actions taken with respect to the body system information. For instance, under the "New Daily Outcomes/Interventions" heading 1310, modifications to body system outcome goals are presented and are categorized by body system (e.g., cardiovascular and neuro). Under the "Orders" area 1312, modifications to medication orders or general orders are presented. Again, the modified orders may be categorized by body system. The user can further input textual information to complete the clinical note 1300. For instance, the user could input information in the "Medical Decision Making" area 1314. Additionally, the clinical note 1300 may also be automatically populated by body-system specific information and/or outcome goals that have been tagged by the user while the user was reviewing the information. Once completed, the signed clinical note 1300 may be stored in association with the patient's electronic medical record.

Figure 9:
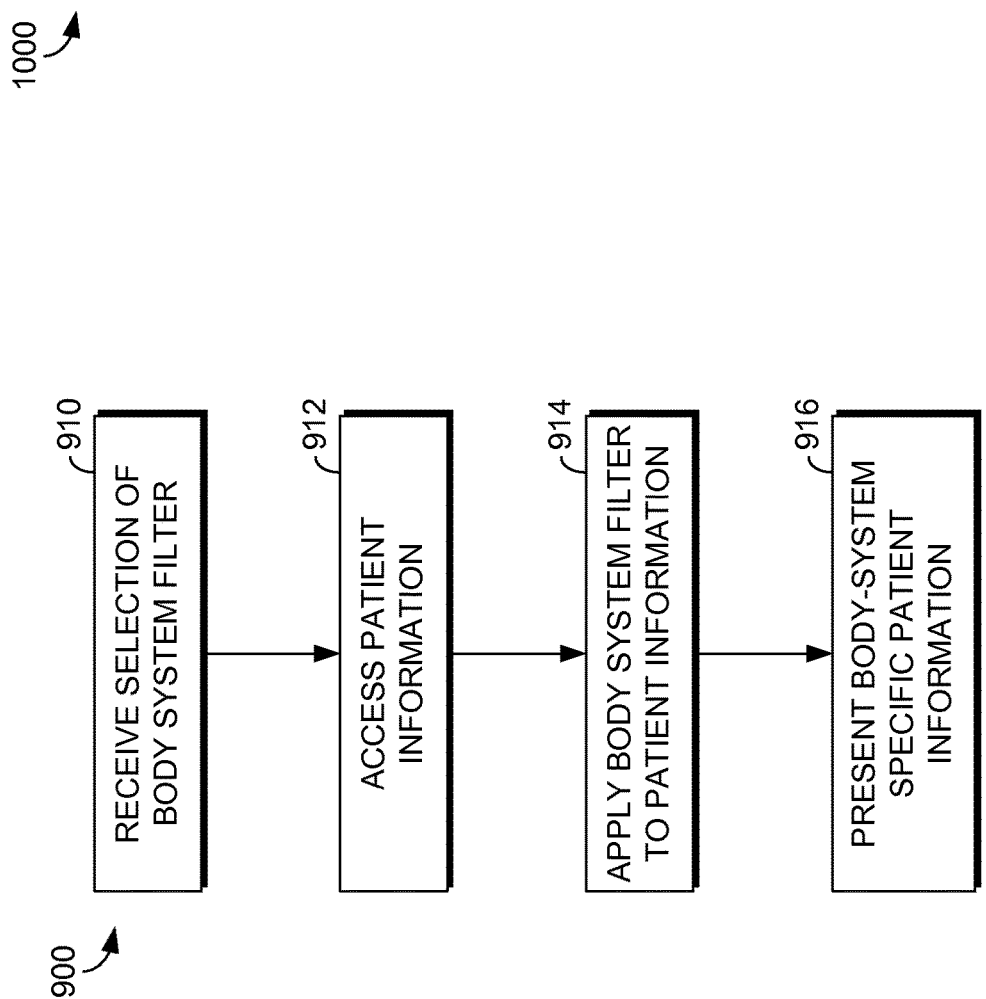

Turning now to FIG. 9, a flow diagram is depicted of an exemplary method 900 of sorting and presenting a patient's medical information by body system. At a step 910, a selection of at least one body system filter directed to a first body system is received from, for example, a clinician involved in the care of the patient. The body system filters include filters directed to the following body systems: neurological, cardiovascular, lungs, renal-fluid, GI-nutrition, integument, musculoskeletal, endocrine, hematology, inflammation, immunocompromised, oncology, mental health, and the like. Further, the body system filter may be configurable by the user.

At a step 912, a patient's medical information stored in association with an EMR is accessed. The medical information includes a wide range of information about such things as lab values, clinical observation information, exam results, and orders including medication and non-medication orders. The medical information may also include outcome goals that are targeted toward helping the patient achieve a desired medical state. The outcome goals may be specific to the healthcare facility, a clinician, and/or may include standardized outcome goals promulgated by medical governing bodies.

At a step 914, the selected body system filter is applied to the patient's medical information to generate a set of body-system specific patient information and outcome goals. The information may include clinical observation information related to the selected body system, physiologic information related to the selected body system, laboratory result information related to the selected body system, medication order information related to the selected body system, non-medication order information related to the selected body system, outcome goals related to the selected body system, and the like.

At a step 916, the set of body-system specific patient information, including outcome goals, is presented on a user interface. The user can interact with the information to modify the information. Modifications can include the addition of body-system specific information, the deletion of information, the suspension of, for example, a medication or non-medication order, and changing the body-system specific information. Any modifications made to the body-system specific patient information are reflected in a summary page. The summary page may summarize modifications made across all body systems, or separate summary pages may be generated for each body system. Further, an electronically signed clinical note may be generated that reflects any modifications made to the body-system specific patient information. The clinical note may also include user-inputted information as well as information that was tagged by the user while viewing the body-system specific patient information. Upon review by a clinician, the clinical note may be completed and stored in association with the patient's electronic medical record.

Figure 10:
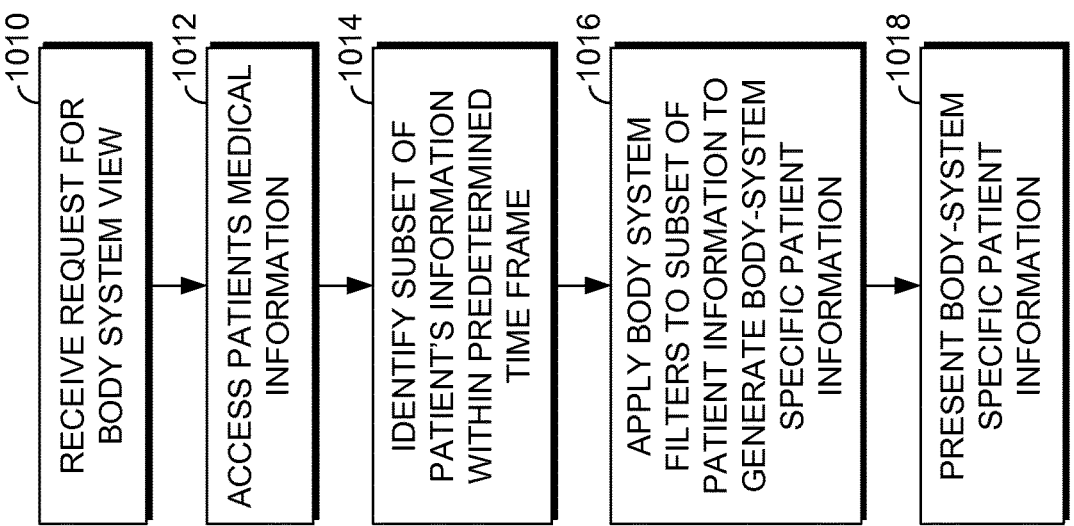
FIGS. 9-10 are flow diagrams illustrating exemplary methods of sorting and presenting patient information by body system in accordance with embodiments of the present invention.

FIG. 10 depicts a flow diagram of an exemplary method 1000 of presenting a patient's medical information in a body system view. At a step 1010, a request for a body system view of the patient's medical information is received from, for example, a clinician caring for the patient. At a step 1012, the patient's medical information is accessed from an EMR, and, at a step 1014, a subset of the patient's information that falls within a predetermined time frame is identified. A standard predetermined time frame of 24 hours may be used, or, alternatively, the user can select a different time frame. For instance, the user may select a shorter time frame if information is rapidly changing or a longer time frame if the information is slowly changing.

At a step 1016, a plurality of body system filters are applied to the subset of the patient's medical information to generate a plurality of sets of body-system specific patient information. Each body system filter is directed to a different body system although data items directed to a first body system may overlap with data items directed to a second body system. For example, a medication may be used to treat multiple, different body systems. This medication would be included within the appropriate sets of body-system specific patient information directed towards those multiple, different body systems.

At a step 1018, the plurality of sets of body-system specific patient information is presented on a user interface. A user is able to select a particular set of body-system specific patient information by utilizing body system filter tabs on the user interface. As mentioned above, the user is able to interact with the information in a variety of ways including accessing detail views, additional information, trending displays, trending graphs, summary pages, and the like.

Figure 11:
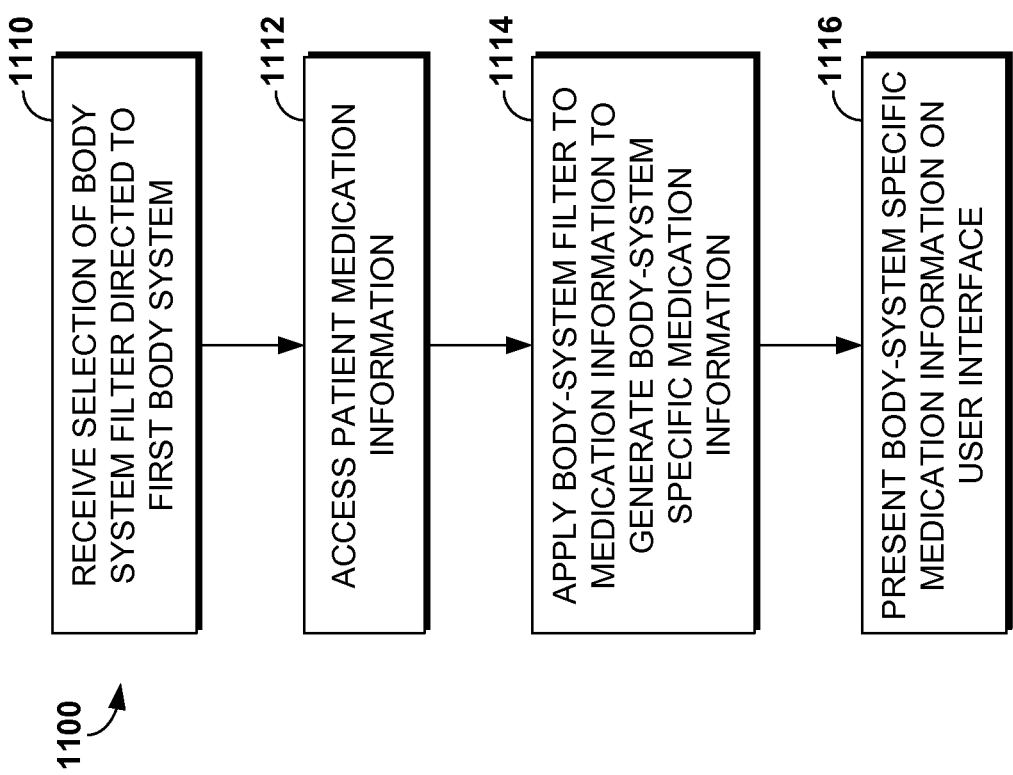

Turning to FIG. 11, a flow diagram is depicted of an exemplary method 1100 of sorting and presenting a patient's medication order information by body system. At a step 1110, a selection of at least one body system filter directed to a first body system is received. At a step 1112, the patient's medication order information stored in association with the patient's EMR is accessed. The medication order information may include information concerning current medication orders in effect for the patient. The information may include medication name, dosage, dosage frequency, route of administration, ordering clinician, order date/time, when the medication order is set to expire, clinician comments, and the like.

At a step 1114, the selected body-system filter is applied to the patient's medication order information to generate a set of body-system specific medication order information. A medication order may be included in more than one set of body-system specific medication order information if that medication is used in the treatment of more than one body system.

At a step 1116, the set of body-system specific medication order information is presented on a user interface. The medication order information may be presented in association with a variety of user action icons and/or status icons. User action icons enable a user to, for example, suspend, modify, or cancel a medication order. User action icons also enable a user to tag a medication order and use the tagged information in a clinical note. Status icons are presented in association with a medication order to indicate that the medication order has been modified in some manner. If a medication order encompasses more than one body system, any changes made to the medication order in a first body system will be reflected in the additional body-system specific medication order views. For example, the status icon would persist in the other body system views indicating that the order has been modified.

Figure 12:
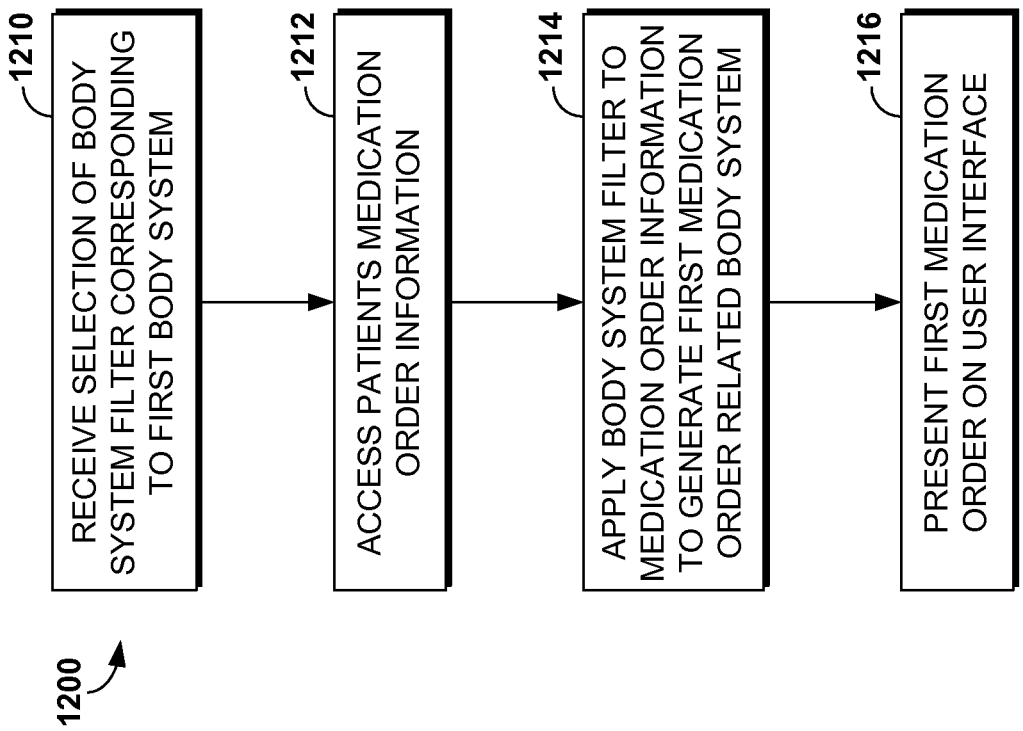
FIGS. 11-12 are flow diagrams illustrating exemplary methods of sorting and presenting a patient's medication order information by body system in accordance with embodiments of the present invention.

Turning to FIG. 12, a flow diagram is depicted of an exemplary method 1200 of presenting a patient's medication order information in a body system view. At a step 1210, a selection of a first body system filter corresponding to a first body system is received. A user may make a selection from a plurality of body system filter tabs on a body system view user interface. At a step 1212, the patient's medication order information in the patient's EMR is accessed, and, at a step 1214, the first body system filter is applied to the patient's medication order information to generate a first medication order related to the first body system. A medication order is related to a body system if it used in the treatment of some condition affecting the body system. At a step 1216, the first medication order is presented on the body system view user interface.

The method 1200 may further comprise receiving a selection of a second body system filter corresponding to a second body system. Again, the selection may be received by a user selecting a body system filter tab on the body system view user interface. The patient's medication information is again accessed, and the second body system filter is applied to the medication order information to generate a second medication order related to the second body system. The second medication order may be different from the first medication order, or the second medication order may be the same as the first medication order if that medication is used in the treatment of more than one body system. The second medication order is presented on the body system view user interface. Both the first and second medication orders may be presented with additional body-system specific patient information as outlined above with respect to FIGS. 9 and 10.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer storage media having computer-executable instructions embodied thereon that, when executed, perform a method for displaying on a graphical user interface (GUI) presented by an end-user computing device, a comprehensive view of a patient's medical information that is specific to a selected body system of a plurality of body systems of the patient, in order to facilitate treatment of medical problems involving at least two different body systems, the method comprising:

displaying on the GUI, by a server communicating with the end-user computing device via a computer network, a tab selection area including a plurality of body system filter tabs, wherein each body system filter tab in the plurality of body system filter tabs represents a particular body system filter for a particular body system of the patient;

receiving, by the server, a selection of a first body system filter tab representing a first body system filter for a first body system of the patient;

accessing from a data store, by the server, medical information comprising one or more medication orders and outcome goals of the patient;

applying, by the server, the first body system filter to the medical information of the patient and the outcome goals generating a first set of current information comprising the medical information related to the first body system of the patient, a first set of current orders comprising the one or more medication orders related to the first body system of the patient, and a first set of outcome goals comprising the outcome goals related to the first body system of the patient;

determining, by the server, an unmet outcome goal based on a comparison of the first body system filter applied to the medical information and the outcome goals;

rendering on the GUI, by the server, simultaneously with the tab selection area, a graphical representation of a comprehensive view of the medical information of the patient related to the first body system of the patient, comprising the first set of current information in a current state display area, the first set of current orders in an order display area, the first set of outcome goals, and a representation of the unmet outcome goal in an outcome goals display area, wherein the order display area includes one or more user action icons corresponding to each of the one or more medication orders of the set of the first set of current orders, and wherein when selected, the one or more user action icons initiate one or more actions related to the corresponding one or more medication orders and change a status of the corresponding one or more medication orders;

upon receiving selection of at least one of the one or more user action icons from the end-user computing device, the server, initiating the selected one or more actions related to the corresponding one or more medication orders, storing in the data store the corresponding one or more medication orders that was acted upon, and changing the status of the corresponding one or more medication orders in one of the first body system filter tab or a second body system filter tab on the GUI;

determining, by the server, that the status of at least one of the one or more medication orders has been changed in one of the first body system filter tab or the second body system filter tab on the GUI; and rendering, by the server, in the order display area on the GUI, one or more status icons corresponding to the one or more medication orders based on the determined status change, wherein the one or more status icons indicate that the corresponding one or more medication order been changed.

2. The one or more non-transitory computer storage media of claim 1, wherein the first set of current information comprises data items related to clinical observation information, physiologic information, and laboratory results information.

3. The one or more non-transitory computer storage media of claim 2, wherein one or more of the data items related to the clinical observation information, the physiologic information, and the laboratory results information are taggable by a user, and wherein the user-tagged data items are used, in part, to create a clinical note.

4. The one or more non-transitory computer storage media of claim 1, wherein the first set of current information represents clinical observation information, physiologic information, and laboratory results information collected over the previous 1000 hours.

5. The one or more non-transitory computer storage media of claim 1, wherein the current state display area is selectable, and wherein selection of the current state display area initiates presentation of trending information related to the first set of current information.

6. The one or more non-transitory computer storage media of claim 5, wherein the trending information comprises the first set of current information over the past 24 hours.

7. The one or more non-transitory computer storage media of claim 1, wherein the first set of current orders further comprises non-medication orders.

8. The one or more non-transitory computer storage media of claim 7, wherein the non-medication orders include laboratory and procedural orders.

9. The one or more non-transitory computer storage media of claim 1, wherein the order display area is selectable, and wherein selection of the order display area initiates presentation of an order action display screen configurable to receive one or more user actions corresponding to at least one current order of the first set of current orders.

10. The one or more non-transitory computer storage media of claim 9, wherein the one or more user actions comprise at least one of a modify action, a suspend action, and a cancel action.

11. The one or more non-transitory computer storage media of claim 1, wherein one or more current orders of the first set of current orders are taggable by a user and are used to create, in part, a clinical note.

12. The one or more non-transitory computer storage media of claim 1, the method further comprising:

displaying on the GUI, a summary display area configured to present a summary of user actions taken with respect to one or more of the first set of current information, the first set of current orders, and the first set of outcome goals.

13. The one or more non-transitory computer storage media of claim 1, wherein the first set of outcome goals represents a desired state of the patient.

14. The one or more non-transitory computer storage media of claim 1, wherein the plurality of body system filter tabs comprises one or more selected from the following:
(A) neurological,
(B) cardiovascular,
(C) lungs,
(D) renal-fluid,
(E) GI-nutrition,
(F) integument,
(G) musculoskeletal,
(H) endocrine,
(I) hematology,
(J) inflammation, and
(K) immunocompromised.

15. A system for displaying a comprehensive view of a patient's medical information that is specific to a selected body system of a plurality of body systems of the patient, in order to facilitate treatment of medical problems involving at least two different body systems, comprising:
- a tab selection area including a plurality of body system filter tabs, wherein each body system filter tab in the plurality of body system filter tabs represents a particular body system filter for a particular body system of the patient,
- a graphical user interface (GUI) presented by an end-user computing device configured to display the tab selection area, and receive a selection of a first body system filter tab representing a first body system filter for a first body system of the patient,
- a processor communicating with the end-user computing device via a computer network configured to perform a method comprising:
- in response to receiving the selection, applying the first body system filter to the medical information of the patient and a first set of outcome goals generating a first set of current information comprising the medical information related to the first body system of the patient, and the first set of outcome goals comprising an outcome goal related to the first body system of the patient,
- determining an unmet outcome goal based on a comparison of the first body system filter applied to the medical information and the first set of outcome goals,
- generating a comprehensive view of the medical information of the patient displayed simultaneously with the tab selection area, the comprehensive view comprising the first set of current information in a current state display area, a first set of current orders in an order display area, the first set of outcome goals and a representation of the unmet outcome goal in an outcome goals display area, wherein the order display area includes one or more user action icons corresponding to each of the one or more medication orders of the set of the first set of current orders, and wherein when selected, the one or more user action icons initiate one or more actions related to the corresponding one or more medication orders and change a status of the corresponding one or more medication orders;
- upon receiving selection of at least one of the one or more user action icons from the end-user computing device, the server, initiating the selected one or more actions related to the corresponding one or more medication orders, storing in a data store the corresponding one or more medication orders that was acted upon, and changing the status of the corresponding one or more medication orders in one of the first body system filter tab or a second body system filter tab on the GUI;
- determining that the status of at least one of the one or more medication orders has been changed in one of the first body system filter tab or the second body system filter tab on the GUI; and
- rendering in the order display area on the GUI, one or more status icons corresponding to the one or more medication orders based on the determined status change, wherein the one or more status icons indicate that the corresponding one or more medication order been changed.

* * * * *